United States Patent
Chern et al.

(10) Patent No.: US 9,160,005 B2
(45) Date of Patent: Oct. 13, 2015

(54) MODIFIED MALEIMIDE OLIGOMER, PREPARATION METHOD THEREOF AND COMPOSITION CONTAINING THE SAME

(71) Applicant: Industrial Technology Research Institute, Hsinchu (TW)

(72) Inventors: Chorng-Shyan Chern, Hsinchu (TW); Jing-Pin Pan, Hsinchu (TW); Chang-Rung Yang, Hsinchu (TW); Tsung-Hsiung Wang, Hsinchu (TW); Guan-Lin Lai, Hsinchu (TW); Jung-Mu Hsu, Hsinchu (TW)

(73) Assignee: INDUSTRIAL TECHNOLOGY RESEARCH INSTITUTE, Hsinchu County (TW)

( * ) Notice: Subject to any disclaimer, the term of this patent is extended or adjusted under 35 U.S.C. 154(b) by 239 days.

(21) Appl. No.: 13/908,848

(22) Filed: Jun. 3, 2013

(65) Prior Publication Data
US 2014/0175337 A1   Jun. 26, 2014

(30) Foreign Application Priority Data
Dec. 21, 2012  (TW) ............................. 101148939 A

(51) Int. Cl.
| H01M 4/62 | (2006.01) |
| H01M 4/13 | (2010.01) |
| C07D 207/452 | (2006.01) |
| C08G 61/02 | (2006.01) |
| C08F 222/40 | (2006.01) |

(52) U.S. Cl.
CPC ........... *H01M 4/623* (2013.01); *C07D 207/452* (2013.01); *C08G 61/02* (2013.01); *H01M 4/13* (2013.01); *H01M 4/622* (2013.01); *H01M 4/625* (2013.01); *C08F 222/40* (2013.01); *C08G 2261/3424* (2013.01); *Y02E 60/122* (2013.01)

(58) Field of Classification Search
CPC ....... H01M 8/1039; H01M 4/13; H01M 4/06; H01M 10/052; H01M 10/0565; H01B 1/122; C08J 5/20; C08J 5/2256; C08G 5/48; C07D 207/452
USPC ........ 252/182.1; 249/217; 430/285.1; 521/27
See application file for complete search history.

(56) References Cited

U.S. PATENT DOCUMENTS

| 4,853,449 A | 8/1989 | Domeier |
| 8,101,669 B2 * | 1/2012 | Pan et al. ......................... 521/27 |
| 8,137,838 B2 * | 3/2012 | Yang et al. .................... 429/217 |
| 2002/0086239 A1 * | 7/2002 | Chen et al. ................. 430/285.1 |
| 2007/0141461 A1 | 6/2007 | Lin et al. |

FOREIGN PATENT DOCUMENTS

| TW | 200828649 | 7/2008 |
| TW | 200828658 | 7/2008 |
| TW | 201023421 A | 6/2010 |
| TW | I332284 | 10/2010 |
| TW | I338964 | 3/2011 |
| TW | 201228070 A1 | 7/2012 |

OTHER PUBLICATIONS

Pan, Jin-Ping et al., Controlling Specially Proprietary Material Promoting Taiwan Listed in the Worlds Powers STOBA Applied on Lithium Ion Batteries,STOBA, Mar. 2010, pp. 5-7.
Pan, Jing-Ping et al., Development and Application of Nano STOBA Material Product, TCIA, Jul. 2011, pp. 47-52.

* cited by examiner

*Primary Examiner* — Khanh Tuan Nguyen
(74) *Attorney, Agent, or Firm* — Muncy, Geissler, Olds & Lowe, P.C.

(57) ABSTRACT

A modified maleimide oligomer is disclosed. The modified maleimide oligomer is made by performing a reaction of a compound having a barbituric acid structure, a free radical capture, and a compound having a maleimide structure. A composition for a battery is also disclosed. The composition includes the modified maleimide oligomer.

20 Claims, No Drawings

MODIFIED MALEIMIDE OLIGOMER, PREPARATION METHOD THEREOF AND COMPOSITION CONTAINING THE SAME

CROSS-REFERENCE TO RELATED APPLICATIONS

This application claims priority to Taiwanese Patent Application No. 101148939, filed on Dec. 21, 2012, the disclosure of which is hereby incorporated by reference herein.

TECHNICAL FIELD

The disclosure relates to a modified maleimide oligomer for a battery, a method for preparing a modified maleimide oligomer and a composition containing a modified maleimide oligomer.

BACKGROUND ART

Recently, 3C electronic devices such as notebook computers, folding cell phones, digital cameras and the like are developed to be lighter, thinner, shorter and smaller, which has become the trend of development of electronic technique and communication devices and further increased the demand for a "secondary battery" as a portable power supply. Accordingly, secondary batteries have been also developed to be thinner, smaller and lighter. Meanwhile, the requirement of capacitance of a secondary battery is increased in response to the need of electronic devices with multifunction, high speed, high performance and high power.

Generally, a lithium ion battery has an energy density about 260 to 270 kWh/m$^3$, which is about 2 folds or higher of the energy density of a nickel-cadmium alkaline secondary battery. Lithium ion/lithium-polymer secondary batteries have the advantages such as rapid charging rate, high discharging power and high energy density, so that lithium ion batteries and lithium-polymer batteries have played important roles in the application of small-scaled electronic devices among all secondary batteries. However, there still is a need to focus on safety, capacitance and cycle life at high temperature and high pressure for batteries in battery industry and electric vehicles.

SUMMARY

The disclosure provides a modified maleimide oligomer for a battery. The modified maleimide oligomer is produced by reacting a compound having a barbituric acid structure, a free radical capture and a compound having a maleimide structure, wherein the reaction mole ratio of the compound having the maleimide structure to the compound having the barbituric acid structure is in a range from 25:1 to 1:1, and the reaction mole ratio of the compound having the barbituric acid structure to the free radical capture is in a range from 1:1 to 1:0.1.

The disclosure further provides a composition for a battery. The composition includes an active material; a conductive additive; a binder; and a modified maleimide oligomer in the amount of 0.1 to 5 wt % based on the total weight of solid contents in the composition.

DETAILED DESCRIPTION OF THE INVENTION

Hereafter, the disclosure will be explained in detail with the reference to certain examples, those skilled in the art can readily understand other advantages and effects of the disclosure according to the contents described in the description.

The modified maleimide oligomer for a battery provided by the disclosure is produced by a partially free radical ring-opening reaction of a compound having a barbituric acid structure, a free radical capture and a compound having a maleimide structure.

In one embodiment, the reaction molar ratio of the compound having the maleimide structure to the compound having the barbituric acid structure is in a range of from 25:1 to 1:1.

The reaction molar ratio of the compound having the barbituric acid structure to the free radical capture is in a range of from 1:1 to 1:01.

The compound having the barbituric acid structure used in the disclosure is a compound of formula (I):

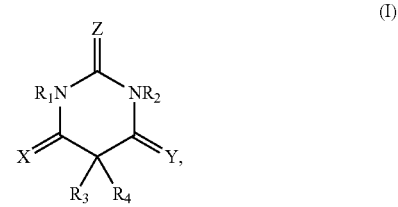

wherein X, Y and Z are all oxygen atoms or at least one of them is replaced with a sulfur atom, and each of $R_1$, $R_2$, $R_3$ and $R_4$ is independently hydrogen or $C_{1-5}$alkyl.

In one embodiment, X, Y and Z are all oxygen atoms, both R3 and R4 are hydrogen, and $R_1$ and $R_2$ are independently hydrogen or a $C_{1-5}$alkyl, provided that $R_1$ and $R_2$ are not hydrogen at the same time.

In a further embodiment, at least one of X, Y and Z is replaced with a sulfur atom, and $R_1$, $R_2$, $R_3$ and $R_4$ are independently hydrogen or $C_{1-5}$alkyl.

The modified maleimide oligomer of the disclosure can be used as an additive in cathode plate slurry, insolating film and electrolyte of a battery such as a lithium ion battery, and the additive contains a compound having a barbituric acid structure which trends to generate free radicals, so that the conductivity would be affected by the excessive free radicals which catch lithium ions. Thus, the modified maleimide oligomer provided in the disclosure is made with the use of a free radical capture, wherein the free radical capture is at least one selected from the group consisting of hydroquinone, α-tocopherol, bisphenol-A, phenol, p-benzoquinone, 1,4-dihydroxynaphthalene, p-methoxyphenol (MEHQ), dodecanethiol, butanethiol, carbon tetrachloride, carbon tetrabromide, catechol, resorcinol, methyl-hydroquinon, trimethylhydroquinone, tert-butylhydroquinone and 2,5-di-tert-butyldroquinone.

The compound having a maleimide structure used in the disclosure may have a dimaleimide structure and/or a monomaleimide structure.

In one embodiment, the compound having a maleimide structure is a compound of formula (II):

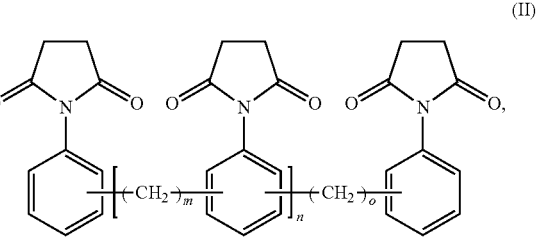

wherein each of m, n and o is an integer greater than 1.

In another embodiment, the compound having the maleimide structure is a compound of formula (III):

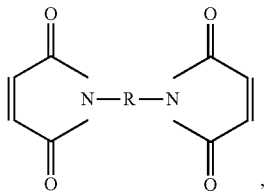

wherein R is $C_{1-12}$alkylene,

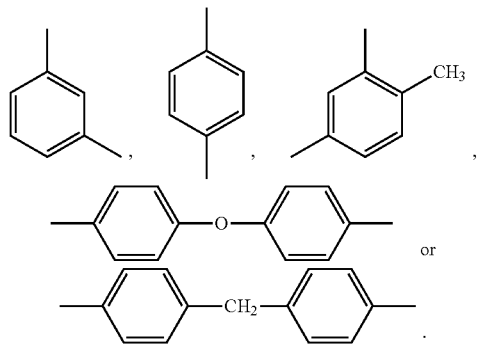

In one embodiment, the $C_{1-12}$alkylene may be —$(CH_2)_2$—, —$(CH_2)_6$—, —$(CH_2)_8$—, —$(CH_2)_{12}$— or —$CH_2$—$C(CH_3)_2$—$CH_2$—$CH(CH_3)$—$(CH_2)_2$—.

In still another embodiment, the compound having the maleimide structure is at least one selected from the group consisting of following monomaleimides: Phenylmaleimide, N-(p-methylphenyl) maleimide, N-(o-methylpheyl)maleimide, N-(m-methylphenyl)maleimide, N-cyclohexyl maleimide, maleimide, maleimidophenol, maleimidobenzocyclobutene, phosphorus-containing maleimide, phosphonate-containing maleimide, siloxane-containing maleimide, N-(4-tetrahydropyranyl-oxyphenyl)maleimide and 2,6-xylylmaleimide.

For example, propylene carbonate (PC) or N-methylpyrrolidone (NMP) can be used as a solvent in the modification, wherein the ratio of the total weight of the compound having the barbituric acid structure, the free radical capture and the compound having the maleimide structure to the weight of the solvent is within the range from 3:97 to 40:60. The modification can be performed at the temperature from 110° C. to 130° C. for 2 to 7 hours.

The modified maleimide oligomer has a dendrimer-like hyperbranched structure which can form a stable complex compound with an electrode active material such as metal oxide in the electrode slurry to increase dispersibility, to reduce viscosity of the slurry, and to maintain the stable viscosity for long time.

In one embodiment, the disclosure provides a composition for a battery. The composition includes an active material; a conductive additive; a binder; and a modified maleimide oligomer in an amount of 0.1 to 5 wt % based on the total weight of the solid contents in the composition, wherein the active material is a cathode active material or an anode active material.

When used as an electrode slurry composition, it can be used in the fabrication of a cathode film of a lithium ion battery or a lithium-polymer battery. In the fabrication of a cathode film, a cathode active material, for example, at least one selected from the group consisting of lithium nickel cobalt aluminum (NCA), lithium nickel cobalt manganese (LNCM), lithium cobalt oxide ($LiCoO_2$), lithium manganese oxide ($LiMnO_2$), lithium nickel oxide ($LiNiO_2$) and lithium ferric phosphate oxide ($LiFePO_4$) is used as the electrode active material in the slurry composition. On the other hand, an anode material such as at least one selected from the group consisting of mesophase carbon microbeads (MCMB) and natural graphite powder is used as the electrode active material in the slurry composition.

The amount of the active material used is not specifically restricted, but it should be enough to provide capacitance needed without affecting processing properties of the electrode film. In one embodiment, the amount of the active material is 20 to 80 wt % based on the total weight of the composition.

The conductive additive of the composition may be, but not limited to, at least one of granular graphite KS4 (4 μm), granular graphite KS6 (6 m), vapor grown carbon fiber (VGCF) and particular carbon black (SP). Preferably, the conductive additive is vapor grown carbon fiber (VGCF).

A functional group can be introduced to the conductive additive by surface treatment such that the conductive additive has a double-bond functional group for reacting with maleimide on its surface. For example, a siloxane coupling agent or an oleic acid coupling agent can be utilized to modify the conductive additive so as to make the conductive additive have a vinyl double-bond functional group for reacting with a modified maleimide disperser on its surface. In general, the amount of the conductive additive is 0.1 to 5 wt % based on the total weight of the composition.

The binder in the composition may be, but not limited to, poly(vinylidene difluoride) (PVDF), acrylic resin or styrene-butadiene rubber (SBR), and at least one binder can be used. The binder and the modified maleimide disperser can be mixed into a uniform network structure to improve the coating properties of the slurry. In one embodiment, the binder is 0.1 to 15 wt % based on the total weight of the composition. The electrode slurry composition may further include other additives such as surfactants; and a reaction initiator such as peroxides or 2,2'-azobisisobutyronitrile (AIBN).

EXAMPLES

Preparation 1

Preparation of a Modified Maleimide Oligomer Containing a Free Radical Capture

Bismaleimide(N,N'-bismaleimide-4,4'-diphenylmethane), barbituric acid (BTA) and hydroquinone at a molar ratio of 2.0:1.0:0.2 were placed in a reactor containing N-methylpyrrolidone (NMP) as a solvent. The ratio of the total weight of bismaleimide, barbituric acid (BTA) and hydroquinone to the weight of the solvent is 20:80. The reaction of the mixture was performed at 130° C. for about 3 hours to obtain a modified maleimide oligomer containing hydroquinone.

Comparative Preparation 1

Preparation of Modified Maleimide Oligomer without Radical Capture

A modified maleimide oligomer was prepared by the method of Example 1, except that no hydroquinone was added.

Example 1

Preparation of Lithium Ion Battery Containing the Maleimide Oligomer of Preparation 1

1087.7 g of lithium cobalt oxide ($LiCoO_2$), 71.7 g of conductive graphite (KS6), 35.9 g of poly(vinylidene difluoride) (PVDF) and 460 g of N-methylpyrrolidone were placed into a 3D mixer to form a cathode slurry of a standard lithium ion battery. The maleimide oligomer of Preparation 1 was 1 wt % based of the total weight of solid contents added in the slurry composition.

Then, a cathode plate was manufactured according to the standard manufacture method of a lithium ion battery. 1,860 g of mesocarbon microbeads (MCMB 2528), 20 g of conductive graphite (KS4), 120 g of poly(vinylidene difluoride) (PVDF), 4.5 g of oxalic acid and 1,451.5 g of N-methylpyrrolidone were placed in a 3D mixer to form a cathode plate slurry which was then coated on a surface of an aluminum foil. A cathode plate was thus obtained.

Further, anode slurry and an anode plate were manufactured according to the standard manufacture method of a lithium ion battery. 1,860 g of mesocarbon microbeads (MCMB 2528), 20 g of conductive graphite (KS4), 120 g of poly(vinylidene difluoride) (PVDF), 4.5 g of oxalic acid and 1,451.5 g of N-methylpyrrolidone were placed in a 3D mixer to form an anode plate slurry which was then coated on a surface of a copper foil. An anode plate was thus obtained.

Then, the cathode plate and the anode plate were assembled to form a standard battery cell (Jelly Roll, 503759C) having the size of 5 mm (height)×37 mm (width)×59 mm (length). 4.2 g of standard electrolyte (PC/EC(ethylene carbonate)/DEC(diethyl carbonate)=2/3/5 (volume ratio) was charged in the battery cell, and 1.1 M LiPF6 and 2.0 wt % vinylene carbonate (VC) were added. Then, the lithium ion battery of Example 1 was yielded after packaging and aging.

Comparative Example 1

Preparation of Ion Battery without the Maleimide Oligomer of Preparation 1

A lithium ion battery was prepared by the method of Example 1, except that the maleimide oligomer of Comparative Preparation 1 was used.

Comparative Example 2

Preparation of Lithium Ion Battery without the Maleimide Oligomer

A lithium ion battery was prepared by the method of Example 1, except that no maleimide oligomer was added.

Test Example 1

Test of Properties of Lithium Ion Batteries

Evaluation of battery properties was carried out under a stable current program at IC discharging/charging rate. The first discharge capacity, the resistance, the discharge residual (the discharged capacity after the last charging) after 500 discharging/charging cycles (each including complete discharging in an hour followed by charging for an hour) at the room temperature, and the discharge residual after 500 discharging/charging cycles at 55° C. were recorded during the test, and the results were listed in Table 1.

TABLE 1

| | Battery Properties | | | |
| --- | --- | --- | --- | --- |
| | The first discharge capacity (mAh) | resistance (mΩ) | 1C/1C discharge residual at room temperature (%) | 1C/1C discharge residual at 55° C. (%) |
| Example 1 | 1348 | 30 | 91 | 84 |
| Comparative Example 1 | 1310 | 33 | 89 | 75 |
| Comparative Example 2 | 1345 | 30 | 86 | 70 |

Room temperature: 20 to 30° C.

Test Example 2

Test of Safety of Lithium Ion Batteries

A needling test was carried out with a needle diameter of 2.5 mm and a needling speed of 1 mm/S to determine safety of the batteries. The results were listed in Table 2.

TABLE 2

| | Bursting into flames | Central Temperature at needle (° C.) |
| --- | --- | --- |
| Example 1 | No | 135 |
| Comparative Example 1 | No | 145 |
| Comparative Example 2 | Yes | 701 |

In light of Table 1 and Table 2, the lithium ion battery prepared from a modified maleimide oligomer containing a free radical capture has safety, high capacitance, and excellent cycle life at both room temperature and high temperature.

The examples aforementioned are used only to illuminate the mechanism and effects of the disclosure, and have no trend to limit the disclosure in any means. Those skilled in the art can modify the examples without departing from the spirits and scopes of the disclosure. Thus, what is claimed by the disclosure are as following claims.

What is claimed is:

1. A method for preparing a modified maleimide oligomer for a battery, comprising the step of:
   performing a reaction of a compound having a barbituric acid structure, a free radical capture, and a compound having a maleimide structure,
   wherein a molar ratio of the compound having the maleimide structure to the compound having the barbituric acid structure is in a range of from 25:1 to 1:1, and a molar ratio of the compound having barbituric acid structure to the free radical capture is in a range of from 1:1 to 1:0.1.

2. The method of claim 1, wherein the compound having the barbituric acid structure has is a compound of formula (I):

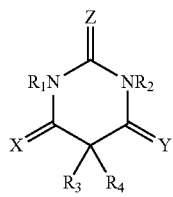

(I)

wherein X, Y and Z are all oxygen atoms or at least one of them is replaced with a sulfur atom, and $R_1$, $R_2$, $R_3$ and $R_4$ are each independently hydrogen or $C_{1-5}$alkyl.

3. The method of claim 2, wherein X, Y and Z are all oxygen atoms, both $R_3$ and $R_4$ are hydrogen, and $R_1$ and $R_2$ are each independently hydrogen or $C_{1-5}$alkyl, provided that $R_1$ and $R_2$ are not hydrogen at the same time.

4. The method of claim 1, wherein the free radical capture is at least one selected from the group consisting of hydroquinone, α-tocopherol, bisphenol-A, phenol, p-benzoquinone, 1,4-dihydroxynaphthalene, p-methoxyphenol (MEHQ), dodecanethiol, butanethiol, carbon tetrachloride, carbon tetrabromide, catechol, resorcinol, methyl-hydroquinon, trimethylhydroquinone, tert-butylhydroquinone and 2,5-di-tert-butyldroquinone.

5. The method of claim 1, wherein the compound having the maleimide structure is a compound of formula (H):

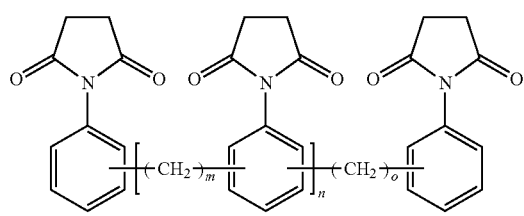

(II)

wherein each of m, n and o is an integer greater than 1.

6. The method of claim 1, wherein the compound having the maleimide structure is a compound of formula (III):

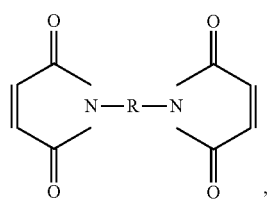

(III)

wherein R is $C_{1-12}$alkylene,

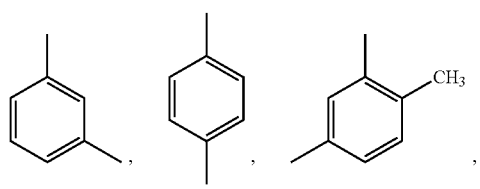

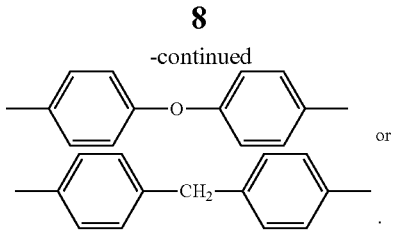

or

7. The method of claim 1, wherein the compound having the maleimide structure is at least one selected from the group consisting of phenylmaleimide, N-(p-methylphenyl) maleimide, N-(o-methylphenyl) maleimide, N-(m-methylphenyl) maleimide, N-cyclohexyl maleimide, maleimide, maleimidophenol, maleimidobenzocyclobutene, phosphorus-containing maleimide, phosphonate-containing maleimide, siloxane-containing maleimide, N-(4-tetrahydropyranyl-oxyphenyl)maleimide and 2,6-xylyl-maleimide.

8. A modified maleimide oligomer for a battery, which is produced by the method of claim 1.

9. A composition for a battery, comprising:
  an active material;
  a conductive additive;
  a binder; and
  the modified maleimide oligomer produced by the method of claim 1 in an amount of 0.1 wt % to 5 wt % based on a total weight of solid contents in the composition.

10. The composition of claim 9, wherein the active material is a cathode active material or an anode active material.

11. The composition of claim 10, wherein the cathode active material is at least one selected from the group consisting of lithium nickel cobalt aluminum, lithium nickel cobalt manganese, lithium cobalt oxide, lithium manganese oxide, lithium nickel oxide and lithium ferric phosphate oxide.

12. The composition of claim 10, wherein the anode active material is at least one selected from the group consisting of mesocarbon microbeads and natural graphite powder.

13. The composition of claim 9, wherein the active material is in an amount of 20 to 80 wt % based on the total weight of the composition.

14. The composition of claim 9, wherein the conductive additive is at least one selected from the group consisting of granular graphite, vapor grown carbon fiber, and carbon black.

15. The composition of claim 9, wherein the conductive additive is surface-treated to have a functional group with a double-bond.

16. The composition of claim 9, wherein the conductive additive is modified by a coupling agent to have a vinyl group.

17. The composition of claim 16, wherein the coupling agent is at least one selected from the group consisting of a siloxane coupling agent and an oleic acid coupling agent.

18. The composition of claim 9, wherein the conductive additive is in an amount of 0.1 to 5 wt % based on the total weight of the composition.

19. The composition of claim 9, wherein the binder is at least one selected from the group consisting of vinyl difluoride, acrylic resin and styrene-butadiene rubber.

20. The composition of claim 9, wherein the binder is in an amount of 0.1 to 15 wt % based on the total weight of the composition.

* * * * *